US008618018B2

(12) United States Patent　　(10) Patent No.: US 8,618,018 B2
Sauchuk et al.　　(45) Date of Patent: Dec. 31, 2013

(54) CATALYTICALLY ACTIVE COMPONENT FOR THERMAL IONIZATION DETECTORS FOR THE DETECTION OF HALOGEN-CONTAINING COMPOUNDS AND PROCESS FOR PRODUCING AN OXIDE-CERAMIC MATERIAL FOR THE COMPONENT

(75) Inventors: Viktar Sauchuk, Dresden (DE); Peter Otschik, Possendorf (DE); Klaus Eichler, Dresden (DE); Mihails Kusnezoff, Dresden (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 1072 days.

(21) Appl. No.: 12/439,264

(22) PCT Filed: Jul. 30, 2007

(86) PCT No.: PCT/DE2007/001405
§ 371 (c)(1),
(2), (4) Date: Nov. 20, 2009

(87) PCT Pub. No.: WO2008/025320
PCT Pub. Date: Mar. 6, 2008

(65) Prior Publication Data
US 2010/0120611 A1　May 13, 2010

(30) Foreign Application Priority Data
Aug. 29, 2006　(DE) .......................... 10 2006 041 510

(51) Int. Cl.
*B01J 23/04*　(2006.01)
*B01J 23/58*　(2006.01)
*G01N 27/00*　(2006.01)

(52) U.S. Cl.
USPC ............................. 502/330; 422/54; 502/344

(58) Field of Classification Search
None
See application file for complete search history.

(56) References Cited

U.S. PATENT DOCUMENTS 2,652,532 A * 9/1953 Zemany ....................... 324/468
2,795,716 A 6/1957 Roberts (Continued)

FOREIGN PATENT DOCUMENTS

CA　1325101　12/1993
DE　1496090　6/1969

(Continued)

OTHER PUBLICATIONS

Office Action issued in corresponding JP 2009-525913 on Apr. 23, 2012.

(Continued)

*Primary Examiner* — Melvin C Mayes
*Assistant Examiner* — Colin W Slifka
(74) *Attorney, Agent, or Firm* — Millen, White, Zelano & Branigan, P.C.

(57) ABSTRACT

The invention relates to catalytically active components for thermal ionization detectors for the detection of compounds containing halogen which have an improved structure as well as to a manufacturing method for an oxide ceramic sintering material for the components. It is the object of the invention to manufacture catalytically active components for thermal ionization detectors for gas chromatographic applications which are thermally, mechanically and chemically stable in the long term and which have increased sensitivity to the materials to be detected. In this respect, the sintering material should be adjustable in a controllable manner in the ideal parameter required for the detector. It is proposed in accordance with the invention to use an oxide ceramic sintering material for the components which comprises a crystalline phase and an amorphous glass phase, with it being essential to the invention that the amorphous glass phase is formed with 0.1 to 20% by weight of a cesium compound.

16 Claims, 6 Drawing Sheets

Comparison of gas chromatograms of a mixture of 4 chlorinated hydrocarbons with a component without (1) and with (2) cesium.

(56) References Cited

U.S. PATENT DOCUMENTS

| | | | |
|---|---|---|---|
| 4,273,559 A * | 6/1981 | Nelson | 436/154 |
| 4,839,143 A | 6/1989 | Vora | |
| 4,928,033 A | 5/1990 | Spangler | |
| 5,498,548 A | 3/1996 | White et al. | |
| 5,521,098 A | 5/1996 | Hermann | |
| 6,752,964 B1 * | 6/2004 | Grubbs et al. | 422/98 |

FOREIGN PATENT DOCUMENTS

| | | |
|---|---|---|
| DE | 3731649 A1 | 3/1989 |
| GB | 1005338 | 9/1965 |
| GB | 2261534 A | 5/1993 |
| JP | 63-18262 A | 1/1988 |
| JP | 2004-043197 A | 2/2004 |
| WO | 2008025320 R | 1/2008 |

OTHER PUBLICATIONS

Kim S. I. et al. "Cesium Ion Transport Across a Solid Electrolyte-Porous Tungsten Interface." Journal of Vacuum Science and Technology Bd.7, Nr. 311, 1. (May 1, 1989):1806-1809. XP000045608.

* cited by examiner

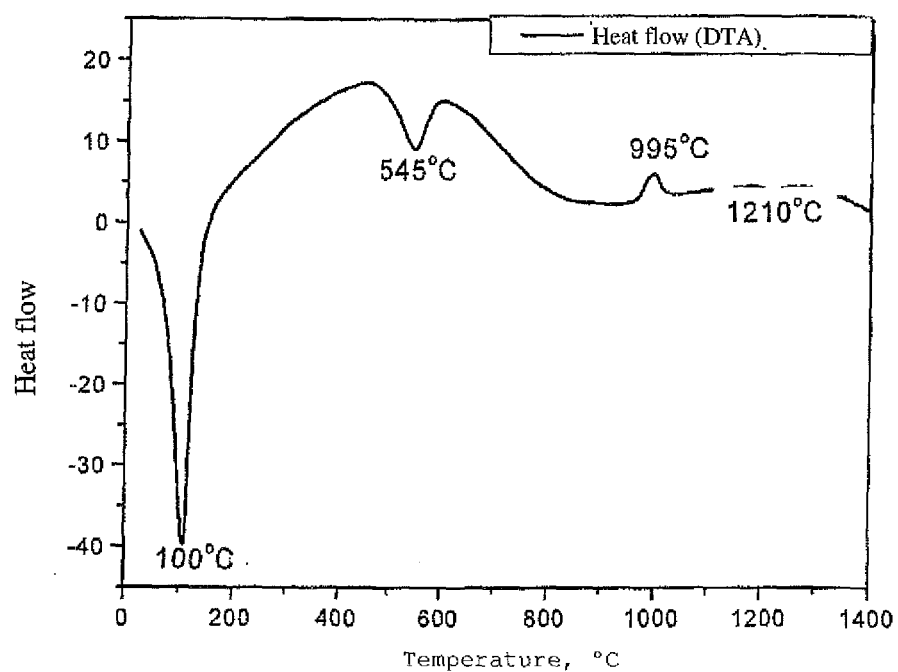
Fig. 1. DTA curve on the sintering of the material.

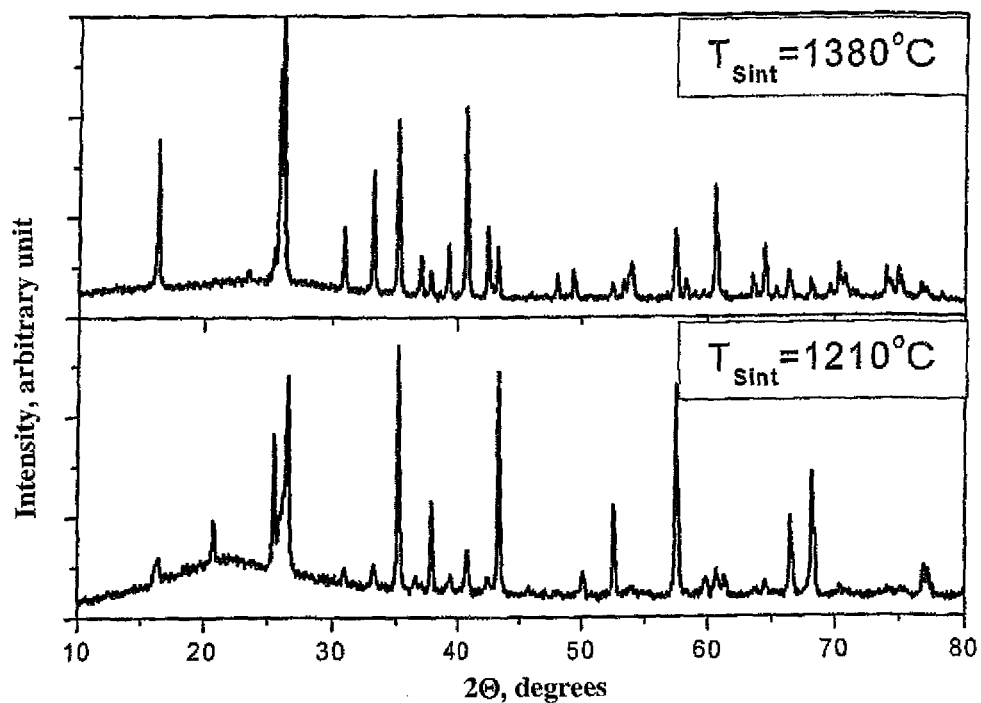
Fig. 2. X-ray diffractograms of the material sintered at different temperatures.

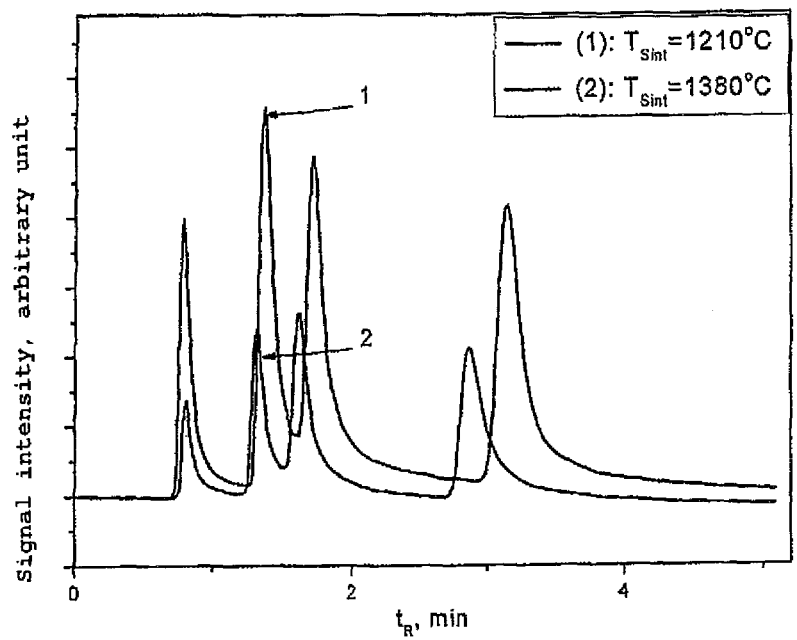
Fig. 3. Comparison of the gas chromatograms of a mixture of 4 chlorinated hydrocarbons with a catalytically active component sintered at different temperatures.

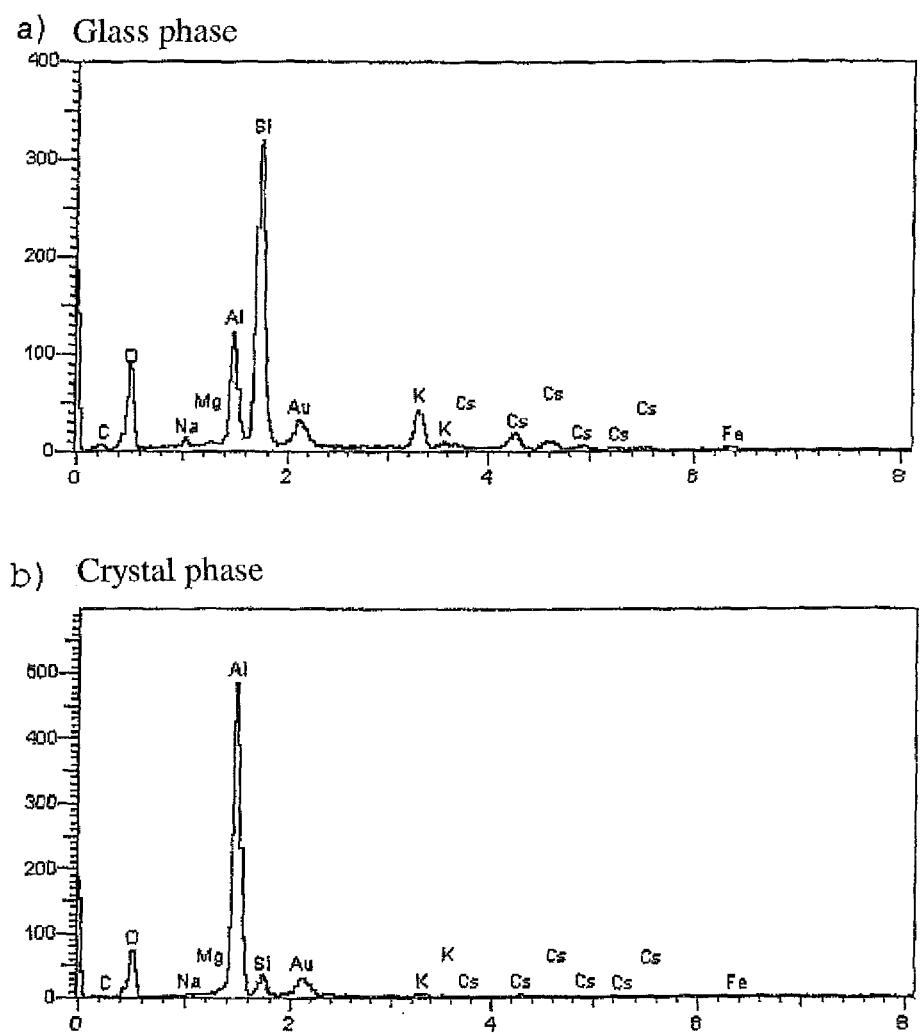
Fig. 4. EDX spectra of the material sintered at 1210°C: a) Glass portion; b) Crystal portion.

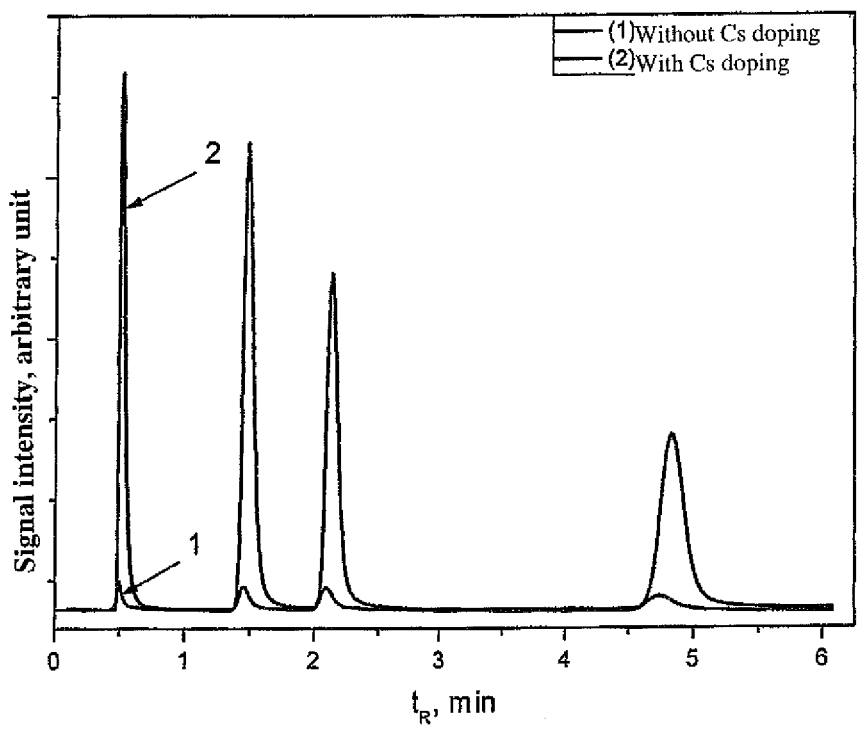
Fig. 5. Comparison of gas chromatograms of a mixture of 4 chlorinated hydrocarbons with a component without (1) and with (2) cesium.

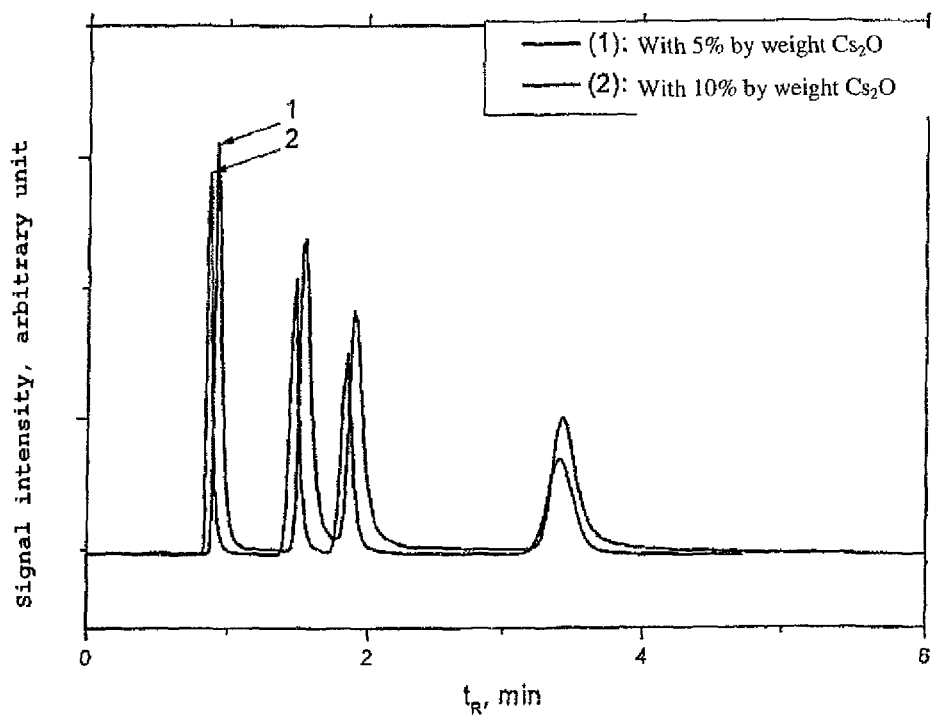
Fig. 6. Comparison of gas chromatograms of a mixture of 4 chlorinated hydrocarbons with the detector with a catalytically active component of the alumina porcelain ceramic C130 sintered at 1210°C and doped with 5% by weight (1) and 10% by weight (2) $Cs_2O$.

CATALYTICALLY ACTIVE COMPONENT FOR THERMAL IONIZATION DETECTORS FOR THE DETECTION OF HALOGEN-CONTAINING COMPOUNDS AND PROCESS FOR PRODUCING AN OXIDE-CERAMIC MATERIAL FOR THE COMPONENT

The invention relates to catalytically active components for thermal ionization detectors for the detection of compounds containing halogens and to a method for the manufacture of an oxide-ceramic material for these components. In this connection, a component is formed from an oxide-ceramic sintered material and is suitable for use in highly sensitive ionization detectors. The oxide-ceramic sintered material has an improved structure with respect to conventional technical solutions.

The component in accordance with the invention is in particular advantageous for detectors in gas chromatography, wherein the material as a catalytically active component of a selective ionization detector is particularly suitable for the detection of compounds containing halogen. The material is used at high temperatures in the range between 700 and 1000° C. In this respect, it is chemically and mechanically stable and is also suitable for the required long-term operation.

An ionization detector is an analytical detection device in which gaseous components are ionized at an elevated temperature and are detected by the ion current which arises.

The nature of the ionization mechanism which runs in these devices has not been definitively clarified to date. One theory is that the ionization of the material to be detected takes place at the surface of the catalytically active component at an elevated temperature. The catalytically active component of the detector is a special material which contains alkali atoms. It is assumed in this respect that the alkali atoms act as catalytically active centers which cause the ionization of the material to be detected.

Different materials and manufacturing technologies for active elements in selective ionization detectors are known from the prior art.

It is thus known (P. L. Patterson, U.S. Pat. No. 4,203,726, May, 1980) to use alumina ceramics with the natural alkali impurities contained therein. However, the problem often results with this material that the required sensor property is only possible for a relatively short operating period. Attempts have been made to counter this disadvantage in that the alumina is saturated with a watery solution which contained an alkali metal salt.

These synthetic alkaline compounds can result in an extended operating period of the element. For instance, synthetic alkali aluminosilicate glasses such as $Li_2O:Al_2O_3:SiO_2=1:1:2$ are used to generate positive ions in ionization detectors. This is in particular successful when the material is heated to temperatures in the proximity of the melting point of the alkali glass (J. P. Blewett, E. J. Jones "Filament Sources of Positive Ions"; Physical Review, 50 (1936) 484).

In 1951, C. W. Rice (U.S. Pat. No. 2,550,948) described an apparatus for the electrical detection of vapors of specific substances in which sodium and potassium silicates $Na_2SiO_3$ und $K_2SiO_3$ as well as synthetic leucites $Li_2O:Al_2O_3:SiO_2=1:1:2$ are proposed as the material.

Alkali sulfates have been found to be particularly suitable for the manufacture of the alkaline active elements. Other types of alkaline compounds which were used are alkali carbonates, alkali halogenides and alkali iodides.

Alkali ceramic mixtures are used for the specific detection of nitrogen and phosphor compounds which comprise 6% by weight $Rb_2SO_4$ and 94% by weight ceramic cement (1st Super Refractory Cement C-10 from Dylon Industries, Inc., Cleveland, Ohio, USA) (P. L. Patterson, U.S. Pat. No. 4,203,726, May/1980)

A substantial disadvantage of detectors using such catalytically active materials is an insufficient sensitivity, which limits their operation and their application possibilities.

To counter this disadvantage of these active elements, materials have been used having a plurality of different alkali metals.

It is furthermore assumed that the amount of alkali metals in the ceramic depends on the designated use of the active ceramic element and can consequently be varied from trace concentrations up to 40% by weight (R. P. White, B. W. Hermann, R. D. Worden, U.S. Pat. No. 5,498,548, March/1996).

P. L. Patterson used a multilayer ionization source in his thermionic detector to ensure both a long operating period and a high sensitivity of the sensor (P. L. Patterson, U.S. Pat. No. 4,524,047, June/1985). In this respect, a multiple of layers are formed on a heating element and each have a different composition to satisfy different functions. Such a multilayer design increases the manufacturing effort and/or cost and causes problems with respect to the adhesion and internal stresses at changing temperatures.

The increased concentration of alkali metals in the material often has the disadvantage that these metals are distributed in an uncontrolled and inhomogeneous manner in the matrix.

In addition, an increase in the alkali metal content usually results in a reduction of the melting point and consequently also in greater alkali evaporation from the surface of the material. Accordingly, active elements with higher alkali contents are restricted in their use at high temperatures by the start of melting.

The increase in the alkali metal concentration in the material also causes a reduction in the mechanical strength and thus in the service life of the element.

It is moreover often difficult to manufacture the synthetic alkaline materials in the same quality so that a reproducibility of the results cannot be reliably ensured on the use of a plurality of detectors.

It is therefore the object of the invention to provide a catalytically active component for thermal ionization detectors for the detection of compounds containing halogen which is thermally, mechanically and chemically stable in the long term and has an increased sensitivity to the materials to be detected.

In this respect, the material used for the components should be able to be adjusted in a controllable manner in the required optimum parameter for the detector. A further object is to provide a corresponding manufacturing method.

The object is solved with respect to the catalytically active component and with respect to the method for the manufacture of the material.

In accordance with the invention, it is thus proposed to provide a catalytically active component formed using oxide ceramic sintered material for thermal ionization detectors which comprises a crystalline phase and an amorphous glass phase, with it being essential for the invention that the amorphous glass phase is formed using 0.1 to 20% by weight of a cesium compound.

It has surprisingly been found that a considerable increase in the sensitivity of a corresponding detector which is manufactured from the oxide ceramic sintered material in accordance with the invention is achieved by an admixture of the cesium compound.

It has furthermore been shown that when the content of the cesium compound which contains the oxide ceramic sintered materials rises above 20% by weight, a deterioration of the mechanical strength of the material occurs at the required operating temperatures so that a higher cesium content is disadvantageous. At contents of the cesium compound below 0.1% by weight, no significant increases in the sensitivity are achieved so that a lower limit of 0.1 is fundamental. It has further been shown that even if the oxide ceramic material only contains up to 10% by weight of a cesium compound, still usable properties are achieved with respect to the mechanical strength of the material at the operating temperatures so that this upper limit for the material used in accordance with the invention is preferred.

Furthermore, particles of platinum having a primary particle size in the nano range can be added for the further improvement of the mechanical strength. The service life can thereby also be extended when an increased sensitivity is observed. During the normal operation of a detector, the surface of the component becomes depleted with respect to active catalytic alkali centers during permanent operation at the increased application temperatures as a consequence of evaporation. The sensitivity of the detectors consequently reduces over the operating time. This can be prevented, but at least reduced, by the activating action of the additional platinum nano particles.

Since platinum is chemically neutral, no compounds are formed with the platinum during the sintering process.

The homogeneously distributed nano particles of platinum form centers of disturbance in the sintered ceramic structure. These centers of disturbance promote the migration of the easily movable alkali ions through the material of the component to its surface. Alkali ions which have been removed in advance can thus be replaced in operation at the surface of the component. The service life can thus be extended while observing a sufficient detection sensitivity of thermal ionization detectors by the possible supply of cesium ions to the surface of the component.

With the material used in accordance with the invention for the catalytically active component, the crystalline base is preferably formed of quartz ($SiO_2$), aluminum oxide ($Al_2O_3$), corundum and mullite ($2SiO_2 3Al_2O_3$). A formation of $CsAlSiO_4$ or $CsAlSi_2O_6$ as a secondary phase is also possible.

A proportion of crystalline phase up to 60% by volume may be present. A higher proportion would result in a reduction in the sensitivity in the detection.

For the cesium compounds, in particular the oxide compounds of cesium are preferred and here $Cs_2O$. In the oxide compounds of the cesium, the invention, however, also includes those with a different oxidation stage of $Cs_2O$.

The invention furthermore provides a method for the manufacture of the oxide ceramic sintering material or the catalytically active component.

In accordance with the invention, a procedure is followed such that, in a first stage, a dried aluminum porcelain ceramic mass is manufactured in powder form with a watery solution of the cesium compound. After drying this mass, it is then subjected to a shaping and sintered at a temperature from 1100 to 1400° C.

It is particularly important in this manufacturing process in this respect that the defined sintering temperatures are observed since at low temperatures, i.e. below 1100° C., the mass to be sintered becomes brittle and the sintered molded body shows small sensitivity and a poor reproducibility of the measured results. As the temperature of the sintering treatment of the raw mass increases, its mechanical stability and the ionization properties of the detector improve. The sensitivity of the detector increases with the temperature of the thermal treatment; however, only up to a sintering temperature of 1400° C. Higher temperatures have proved to be unfavorable. It has been shown that it is particularly favorable when the thermal treatment is carried out at 1210° C.±10° C.

At temperatures above 1210° C., the material conversion processes in the material are completed and the proportion of crystal phase in the material then continues to grow. The alkali ions are thereby firmly bound in the material, as e.g. cesium ions in the refractory pollucite $CsAlSi_2O_6$.

The catalytic activity is thereby reduced. As the sintering temperature increases, however, the vapor pressure of the highly volatile alkali components also rises, whereby the concentration of the alkali atoms and consequently also the catalytic activity are also reduced.

From a material view, the method in accordance with the invention includes with respect to the alumina porcelain ceramic masses which are used in powder form all ceramic masses known per se in the prior art, for instance in particular starting materials such as feldspar, kaolin and alumina. With the cesium compounds, in particular cesium carbonate, i.e. a water solution of cesium carbonate, are preferred The weight ratios in which the alumina porcelain ceramic masses are the cesium compound are used are preferably 80% by weight to 99.9% by weight for the alumina porcelain ceramic masses and 0.1 to 20% by weight for the cesium compound with respect to the total mass of the mixture. Platinum nano particles should be used with a portion from 5 to 10% by weight with respect to the dry mass (total starting mass) of the used alumina porcelain ceramic material and of the cesium compound. The powders used should have a mean primary particle size from 50 nm to 100 nm.

Compositions of the invention can further contain fluxes, plasticizers and/or liquefiers.

The invention will be described in more detail in the following with reference to an embodiment and to FIGS. 1 to 6.

Embodiment 1: Manufacture of an oxide ceramic sintering material for catalytically active components:

5.78 g $Ca_2CO_3$, which corresponds to the amount of 5 g $Cs_2O$, is weighed in and dissolved in 50 ml deionized water by stiffing. This solution is mixed with 95 g of a dried ceramic raw material powder C130 (manufacturer DWS-Keramik Neuhaus GmbH, Neuhaus Schiernitz, DE) and homogenized by careful stirring. The homogeneous material is dried at room temperature.

Embodiment 2: Manufacture of an oxide ceramic sintering material additionally activated with platinum for catalytically active components:

95 g dried ceramic raw material powder C103 is mixed in a mixer with 5.263 g powdery platinum. The mixture is added to 50 ml deionized water and 5.78 g $Ca_2CO_3$ dissolved therein and the mixture is homogenized. The mixture was dried at room temperature. The sintering then took place until a maximum sintering temperature of 1210° was reached.

FIG. 1 shows a DTA curve in the sintering process;

FIG. 2 shows an X-ray diffractogram of a material sintered in accordance with the invention;

FIG. 3 shows measured results at different sintering temperatures of the material;

FIG. 4 shows an EDX analysis;

FIG. 5 shows a diagram of the sensitivity of the material in accordance with the invention as an ionization detector in comparison with the prior art; and FIG. 6 shows the sensitivity of a detector in accordance with the invention for different compositions of the material.

It can be illustrated by the DTA curve shown in FIG. 1 that the conversion processes in the material for the component, starting from the raw material, run up to a temperature of 1210° C. so that the thermal treatment on the sintering is particularly favorable at a temperature in the narrow temperature range 1210° C.±10° C.

The X-ray diffractogram of the sintered material in FIG. 2 shows the crystalline phases of quartz ($SiO_2$), aluminum oxide ($Al_2O_3$) and mullite ($2SiO_2 3Al_2O_3$) as well as a substantial portion of glass phase which is important for the function of the component.

The differences in the sensitivity of the detector with the active components sintered at different temperatures are clearly recognizable in FIG. 3. It also follows from FIG. 3 that the ideal sintering temperature of the catalytically active component of the detector is at 1210° C.

It becomes clear from the EDX analysis shown in FIG. 4 that the alkali metals are predominantly distributed in the glass phase of the sintered material so that the catalytic activity of the material is mainly ensured by the glass portion.

An admixture of cesium to the alumina porcelain mass causes a clear increase of sensitivity of a detector with a catalytically active component.

The material used in accordance with the invention is manufactured from a dried alumina porcelain ceramic mass in powder form and a watery solution of cesium carbonate. For this purpose, the watery solution of cesium carbonate is processed with the alumina porcelain ceramic mass to a mush-like mass, is carefully homogenized, dried and molded and finally sintered at a temperature of 1210±10° C.

The diagram in FIG. 5 shows that the material manufactured in accordance with the invention has a sensitivity for halogenated hydrocarbons in an ionization detector 100 times greater than comparison detectors on the same active principle. In this connection, it has the same sensitivity for halogenated hydrocarbons with different numbers of halogen atoms. This indicates that only simply charged ions arise in the gas phase on ionization.

FIG. 6 shows that the sensitivity of a detector is comparable with the catalytically active component for the compositions $C130_{0.95}(Cs_2O)_{0.05}$ and $(C130)_{0.9}(Cs_2O)_{0.1}$.

An increase in the $Cs_2O$ content above 10% by weight results in a deterioration of the mechanical strength of the material at operating temperatures and is therefore disadvantageous.

The invention claimed is:

1. A catalytically active component for thermal ionization detectors for the detection of compounds containing halogens, wherein the component comprises an oxide ceramic sintering material which comprises a crystalline phase and an amorphous glassy phase, with the amorphous glassy phase comprising 0.1 to 20% by weight of a cesium compound and platinum particles in a proportion of 5 to 10% by weight.

2. The component in accordance with claim 1, wherein the amorphous glassy phase is formed using 0.1 to 10% by weight of the cesium compound.

3. The component in accordance with claim 1, wherein the cesium compound is an oxide compound of the cesium.

4. The component in accordance with claim 3, wherein the oxide compound of cesium is $Cs_2O$.

5. The component in accordance with claim 1, wherein the crystalline phase comprises $SiO_2$, $Al_2O_3$, $2SiO_2 3Al_2O_3$, $CsAlSiO_4$ and/or $CsAlSi_2O_6$.

6. The component in accordance with claim 1, further comprising fluxes, plasticizers, and/or liquefiers.

7. The component in accordance with claim 1, wherein the platinum particles have a mean primary particle size from 50 nm to 100 nm.

8. The component in accordance with claim 1, wherein the crystalline phase comprises quartz, corundum and/or mullite.

9. A thermal ionization detector comprising a component according to claim 1.

10. A method for the manufacture of the catalytically active component of claim 1, comprising:
 a) manufacturing a mixture of a powdery alumina porcelain ceramic mass, platinum particles, and a watery solution of a cesium compound;
 b) drying the mixture;
 c) shaping and sintering the dried mixture at 1100° C. to 1400° C.

11. The method in accordance with claim 10, wherein the sintering is carried out at a temperature of 1210±10° C.

12. The method in accordance with, claim 10, wherein the drying (method step b) is carried out at room temperature.

13. The method in accordance with claim 10, wherein the powdery alumina porcelain ceramic mass is feldspar, kaolin, alumina or mixtures thereof.

14. The method in accordance with claim 10, wherein a watery solution of cesium carbonate is used as the cesium compound.

15. The method in accordance with claim 10, wherein 80 to 94.9% by weight of powdery alumina porcelain ceramic mass and 0.1 to 20% by weight of the cesium compound are used in (a).

16. The method in accordance with claim 10, wherein the platinum particles are nano particles.

* * * * *